United States Patent
Kwon et al.

(10) Patent No.: US 8,329,234 B2
(45) Date of Patent: Dec. 11, 2012

(54) MASK PACK COMPRISING COSMETIC COTTON-LIKE MATERIAL PREPARED FROM PAPER MULBERRY

(75) Inventors: Sun Sang Kwon, Yongin-si (KR); Myeong Hun Yeom, Yongin-si (KR); Chang Man Park, Yongin-si (KR); Duck Hee Kim, Seoul (KR); Han Kon Kim, Suwon-si (KR)

(73) Assignee: Amorepacific Corporation, Seoul (KR)

( * ) Notice: Subject to any disclaimer, the term of this patent is extended or adjusted under 35 U.S.C. 154(b) by 0 days.

(21) Appl. No.: 13/131,774

(22) PCT Filed: Nov. 27, 2009

(86) PCT No.: PCT/KR2009/007052
§ 371 (c)(1),
(2), (4) Date: May 27, 2011

(87) PCT Pub. No.: WO2010/062142
PCT Pub. Date: Jun. 3, 2010

(65) Prior Publication Data
US 2011/0230570 A1  Sep. 22, 2011

(30) Foreign Application Priority Data
Nov. 28, 2008 (KR) .................. 10-2008-0119427

(51) Int. Cl.
*A61K 36/00* (2006.01)
*A61K 47/00* (2006.01)
*D21C 9/02* (2006.01)
(52) U.S. Cl. ................. 424/769; 514/783; 162/60
(58) Field of Classification Search .................. None
See application file for complete search history.

(56) References Cited

U.S. PATENT DOCUMENTS
7,045,137 B1  5/2006  Muta et al.

FOREIGN PATENT DOCUMENTS
| KR | 2002-0011960 A | 2/2002 |
| KR | 2003-0072966 A | 9/2003 |
| KR | 10-2004-0015858 A | 2/2004 |
| KR | 10-0760670 B1 | 10/2007 |

OTHER PUBLICATIONS

Zheng et al. (2008) Food Chemistry 106: pp. 529-535.*

* cited by examiner

*Primary Examiner* — Chris R Tate
*Assistant Examiner* — Russell Fiebig
(74) *Attorney, Agent, or Firm* — Sughrue Mion, PLLC

(57) ABSTRACT

The present invention relates to a cosmetic cotton-like material having excellent air permeability that is prepared from the paper mulberry by removing fiber-binding substances such as pectin and lignin from the paper mulberry fiber, a preparation method thereof and a mask pack comprising the cotton-like material.

10 Claims, No Drawings

MASK PACK COMPRISING COSMETIC COTTON-LIKE MATERIAL PREPARED FROM PAPER MULBERRY

CROSS REFERENCE TO RELATED APPLICATIONS

This application is a National Stage of International Application No. PCT/KR2009/007052 filed Nov. 27, 2009, claiming priority based on Korean Patent Application No. 10-2008-0119427, filed Nov. 28, 2008, the contents of all of which are incorporated herein by reference in their entirety.

TECHNICAL FIELD

The present invention relates to a cosmetic cotton-like material having excellent air permeability that is prepared from the paper mulberry by removing fiber-binding substances such as pectin and lignin from the paper mulberry fiber, a preparation method thereof and a mask pack comprising the cotton-like material.

BACKGROUND ART

The main raw material of Korean traditional paper (also referred to as "Hanji") is the paper mulberry (*Broussonetia kazinoki*). Cellulose fibers extracted from the paper mulberry are relatively weak among bast fibers of the same kind and have short lengths. For these reasons, these fibers have been scarcely used for fiber products, have been limited to the production of papers and have been mainly used for the production of Korean traditional paper.

A method for producing Korean traditional paper is described hereafter.

Korean traditional paper has been produced by a paper-forming method comprising the following sequential processes: preparation of raw material; steaming, and drying in sunlight; beating; sheet formation; dewatering; drying; and finishing. Paper mulberry bark consists of a black outer bark and a white inner bark. To remove the black outer bark, that is, to facilitate the removal of the bark, the paper mulberry is first steamed. The boiled bark of the paper mulberry is peeled off to leave the white inner bark. The well-dried white bark is soaked in water for one or two days. The soaked bark is cut to a suitable size and boiled thoroughly in lye for 4-5 hours. Then, the boiled material is washed to remove the lye and dried in sunlight to bleach. Bumps of the washed and bleached material are removed by hand, and then the white bark is placed on a stone mortar and subjected to a beating process in which the paper mulberry fiber is pounded with a club for 40-60 minutes. In this process, the fiber disintegrates, and a thickener is added to the completely disintegrated fiber, which is then stirred well to achieve a uniform consistency.

Next, a sheet-forming process (called "Choji process" in Korean) is performed in which a net-shaped structure is immersed and moved backwards-and-forwards and side-to-side in a container containing the paper mulberry fiber. Although a process employing a single-net-shaped structure ("Oebal Choji") traditionally used for sheet formation in making Korean traditional paper, an improved process employing a twin-net-shaped structure "Ssangbal Choji" has recently been frequently used. The net-shaped structures having a wet sheet laid thereon are stacked on each other with a pillow interposed between the wet sheets, and the wet sheets are pressed to remove water.

Finally, a finishing process is performed. In this process, dilute rice paste is applied to the surfaces of the incompletely dried sheets, which are then stacked in several tens of layers and pounded several hundred times with a wooden roller- or pestle-shaped article to make the sheets compact and smooth and increase the strength and gloss, thus obtaining finished Korean paper.

Recently, the Korean paper making process has been improved by introducing elements of Western paper making technology. A chemical substance such as sodium carbonate or sodium hydroxide is used instead of lye in the process of boiling the white bark. However, when the white bark is boiled with a strong alkaline chemical substance such as sodium hydroxide, a problem arises in that the fiber itself is damaged, resulting in loss of gloss of the resultant Korean paper, decreases in the strength and yield, and a great reduction in the quality. Further applications of Western paper technology include performing the beating process using a knife-type beater so as to increase productivity. Also, the disintegration (pulping) process is performed using a screw, and after the dissociation, a polymer such as polyacrylamide or polyethylene oxide is used as the thickener. In the drying process following the sheet forming process, the formed sheet is dried on an iron plate heated by steam. In addition, the finishing process is performed using a motor.

In the Korean paper making process, if the paper mulberry pulp in the wet state obtained by beating the white bark of the paper mulberry is dried as it is, the fiber becomes very hardened in an entangled state, thus making it substantially impossible to disintegrate the fiber. This is characteristic of bast fibers, wherein substances such as pectin and lignin bind the fibers and fibrous materials to each other in the drying process, thereby hardening the fibers. Such characteristics make the paper mulberry fiber suitable for papermaking, but act as the biggest obstacle to using the paper mulberry fiber in the production of other fiber products. Accordingly, currently, there is little or no product obtained using paper mulberry bast, other than as a raw material for making Korean traditional paper.

DISCLOSURE

Technical Problem

Accordingly, the present inventors have conducted studies to utilize advantageously the characteristics of Korean paper and to enlarge the applicability thereof. As a result, the present inventors have prepared a cosmetic cotton-like material having various excellent properties of the paper mulberry while utilize advantageously the characteristics of Korean traditional paper through the fibrous structure thereof, by using paper mulberry fiber, which is a raw material for making Korean traditional paper, and effectively removing fiber-binding substances such as pectin and lignin from paper mulberry pulp. Further, the present inventors have found that the prepared cotton-like material can be used to prepare a mask pack capable of effectively delivering an active ingredient to the skin, thereby completing the present invention.

Therefore, an object of the present invention is to provide a cosmetic cotton-like paper mulberry material from which fiber-binding substances such as pectin and lignin are effectively removed, and a preparation method thereof.

Another object of the present invention is to provide a mask pack having an excellent skin feel and water-holding capacity that is made using a cosmetic cotton-like paper mulberry material having an excellent skin feel, air permeability and porosity.

Technical Solution

To achieve the above objects, the present invention provides a method for preparing a cosmetic cotton-like material from paper mulberry, the method comprising the steps of: 1) treating the bark of paper mulberry with an alkaline solution to remove the black outer bark from the paper mulberry bark; 2) bleaching the paper mulberry bark, from which the outer bark has been removed, with a bleaching agent, to prepare a white bark; 3) adding an alkaline solution to the white bark and pulping the paper mulberry bast fiber; 4) washing and drying the pulped paper mulberry bast fiber; and 5) hydrolyzing the dried paper mulberry bast fiber with an acid while maintaining the bast fiber at a temperature of 30° C. to 40° C. for more than 48 hours, thus preparing a cosmetic cotton-like material.

The present invention also provides a mask pack comprising a cosmetic cotton-like material prepared according to said method.

Advantageous Effects

The cosmetic cotton-like material according to the present invention has excellent air permeability, which is a characteristic of Korean traditional paper. When the cosmetic cotton-like material is mixed with an aqueous solution of a cosmetic active ingredient to prepare a mask pack, the mask pack can provide a skin-moisturizing effect upon contact with the skin and, furthermore, effectively deliver the active ingredient to the skin.

BEST MODE

Hereinafter, the present invention is described in further detail.

It is generally known that Korean traditional paper prepared from paper mulberry is permeable to air and light and controls humidity. This is because the fine surface of Korean traditional paper has numerous invisible pores, which can provide ventilation and naturally control indoor temperature and humidity.

The present invention relates to a cosmetic cotton-like material made from paper mulberry that has such characteristics, and a preparation method thereof.

The present invention provides a method for preparing a cosmetic cotton-like material from paper mulberry, the method comprising the steps of: 1) pulping the paper mulberry; and 2) powdering the pulped paper mulberry bast fiber.

More specifically, the method for preparing the cosmetic cotton-like material may comprise the steps of:

1) treating the bark of paper mulberry with an alkaline solution to remove the black outer bark from the paper mulberry bark;

2) bleaching the paper mulberry bark, from which the outer bark has been removed, with a bleaching agent, to prepare a white bark;

3) adding an alkaline solution to the white bark and pulping the paper mulberry bast fiber;

4) washing and drying the pulped paper mulberry bast fiber; and 5) hydrolyzing the dried paper mulberry bast fiber with an acid while maintaining the bast fiber at a temperature of 30° C. to 40° C. for more than 48 hours, thus preparing a cosmetic cotton-like material.

In step 2), at least one bleaching agent selected from the group consisting of calcium hypochlorite, sodium hypochlorite and sodium chlorite is added to the prepared paper mulberry bark at a weight ratio of 1:8 to 1:20 relative to the paper mulberry bark to prepare the white bark.

Examples of an alkaline solution that can be used in steps 1) and 3) include aqueous solutions of sodium hydroxide, ammonium hydroxide and copper hydroxide. Herein, to remove substances such as pectin and lignin from the paper mulberry bark and facilitate mixing, the alkaline solution is used at a weight ratio of 1:5 to 1:50, and preferably 1:10, relative to the paper mulberry bark, and the bark-containing solution is stirred with heating at 70-90° C., preferably 80° C., for 4-5 hours. If the amount of weak alkaline solution used is too small compared to the paper mulberry bark, it is difficult to achieve sufficient removal of impurities, and if the amount is too large, the binding strength between the fibers is reduced. Through steps 1) to 3), the inner bark from which fiber-binding substances such as pectin and lignin have been removed can be prepared.

In step 4), the paper mulberry bast fiber from which the fiber-binding substances have been removed and which contains only pure cellulose fibers is washed with water, and then dried in a convection dryer at about 80-90° C.

The paper mulberry bast fiber (i.e. paper mulberry pulp) purified in step 5) is a state from which substances such as hemicelluloses and lignin have been removed. More specifically, the purified paper mulberry pulp contains a high content of alpha-cellulose, contains no lignin and has a relatively low content of hemicelluloses. In the prior art, purified paper mulberry pulp is hydrolyzed in a 50% (w/w) strong alkaline solution at a high temperature of 98° C. to obtain a cotton-like material. The cotton-like material obtained in this prior art process cannot attain the desired properties, because a large portion of the molecular chains of cellulose are decomposed such that the cotton-like material cannot show sufficient hardness suitable for application as a mask pack as aimed for in the present invention.

Accordingly, in order to provide a cotton-like material capable of maintaining hardness suitable for the formulation of a cosmetic mask pack, the present invention suggests hydrolysis conditions different from those of the prior art. Specifically, in the present invention, the purified pulp is hydrolyzed by treatment with an acid in an amount of 5-10 wt % based on the weight of the purified pulp while being maintained at about 30-40° C. for 48-60 hours, and then the collected solid is ground with a mill such as an air-jet mill or a hammer mill, thus preparing a cosmetic cotton-like material. The acid used in the hydrolysis process may be any acid that is conventionally used in the art. Most preferably, the acid is 1-3N hydrochloric acid. The reason is because the hydrolytic activity of hydrochloric acid is the most excellent compared to that of other conventionally used acids, and thus the reaction time can be reduced to maximize the efficiency of the hydrolysis process. If acids other than hydrochloric acid are used, the concentration of the acids and the reaction time may need to be increased, because the acids have reduced hydrolysis activity.

The inventive cosmetic cotton-like material prepared by the above-described method is characterized in that it has excellent air permeability and water-holding capacity.

The present invention also relates to a mask pack prepared by incorporating a skin active ingredient and hydrogel into the cosmetic cotton-like material and a preparation method thereof.

The mask pack according to the present invention can be prepared through the following steps:

1) treating the bark of paper mulberry with an alkaline solution to remove the black outer bark from the paper mulberry bark;

2) bleaching the paper mulberry bark, from which the outer bark have been removed, with a bleaching agent, to prepare a white bark;

3) adding an alkaline solution to the white bark and pulping the paper mulberry bast fiber;

4) washing and drying the pulped paper mulberry bast fiber;

5) hydrolyzing the dried paper mulberry bast fiber with an acid while maintaining the bast fiber at a temperature of 30° C. to 40° C. for more than 48 hours, thus preparing a cosmetic cotton-like material; and 6) mixing the cosmetic cotton-like material with a skin active ingredient to prepare a mask pack.

Steps 1) to 5) of the method for preparing the mask pack are performed in the same manner as those of the method for preparing the cotton-like material.

As the skin active ingredient used in step 6), any ingredient may be used that is conventionally used in the art. Examples of skin active ingredients that can be used in the present invention include, but are not limited to, a wrinkle-reducing ingredient selected from the group consisting of retinol, retinyl palmitate, adenosine, and polyethoxylated retinamide; a skin whitening ingredient selected from the group consisting of arbutin, a paper mulberry extract, a licorice extract, ethyl ascorbyl ether, ascorbyl glucoside, and magnesium ascorbyl phosphate; a moisturizing ingredient selected from the group consisting of *Schizophyllum commune* polysaccharide, niacinamide, and N-acetylglucosamine; and a skin trouble- and keratin-improving ingredient selected from the group consisting of an ivy extract, a fancy extract, a Chamomile extract, and a soybean extract.

In the present invention, the cotton-like material and the skin active ingredient are preferably mixed with each other at a weight ratio of 1:10 to 10:1, most preferably 1:5.

Also, the mask pack according to the present invention may utilize as a support a nonwoven fabric or cotton that are used as supports in existing mask packs. As a raw material for the nonwoven fabric, synthetic fiber such as viscose, rayon or nylon may be used.

Hydrogel has a good water-washing property, is not sticky and is swollen by water or other liquids to exhibit a certain degree of flowability. Due to such properties, hydrogel is suitable for use in formulations. In addition, it has good skin adhesion and can impart a moist feel to the skin.

The mask pack according to the present invention can be prepared by incorporating the above-described skin active ingredient into hydrogel according to any method well known in the art, soaking the cosmetic cotton-like material with the active ingredient-containing hydrogel, and then attaching the cotton-like material to a non-woven fabric.

MODE FOR INVENTION

Hereinafter, the present invention is described in further detail with reference to examples. It is to be understood, however, that these examples are for illustrative purposes only and are not to be construed to limit the scope of the present invention.

EXAMPLE 1

Preparation of Cosmetic Cotton-Like Material

1) Pulping of Paper Mulberry

To bleach the inner bark of paper mulberry, the inner bark was soaked in a 0.5N aqueous solution of calcium hypochlorite at a weight ratio of 1:10, stirred at room temperature for 4 hours, and then washed with sufficient water, thus preparing a white inner bark. Next, the white inner bark was soaked in a 10% (w/v) aqueous solution of sodium hydroxide at a weight ratio of 1:10 and stirred with heating at 80° C. for 4 hours. Through such processes, a pulped inner bark from which paper mulberry fiber-binding substances such as pectin and lignin had been removed was prepared.

2) Preparation of Cosmetic Cotton-Like Material from Paper Mulberry Pulp

The pulped paper mulberry bast fiber and a 2N aqueous solution of hydrochloric acid were mixed at a weight ratio of 1:5, and then stirred using a low-speed stirrer. The stirred material was hydrolyzed while maintained at about 34° C. for 48 hours. Next, the residue was washed with water, and then neutralized with ammonia. The neutralized material was washed again with sufficient water to remove the salt, and then distilled water was added to the residue, thus preparing an about 20% (w/v) dispersion of hydrolyzed plant mulberry fiber. The dispersion of paper mulberry was filtered, and then dried in hot air at 80° C., thus obtaining a solid of paper mulberry fiber. The collected solid was ground with a mill, thus obtaining a cotton-like material.

COMPARATIVE EXAMPLE 1

Preparation of Cotton-Like Material by Alkaline Hydrolysis

A cotton-like material of Comparative Example 1 was prepared according to the same manner as Example 1, except that a same amount of potassium persulfate was used instead of the 2N aqueous solution of hydrochloric acid used in the hydrolysis process of Example 1.

TEST EXAMPLE 1

Measurement of Hardness

The hardness of each of the cotton-like materials prepared in Example 1 and Comparative Example 1 was measured, and the measurement results are shown in Table 1 below. The measurement was carried out using 14 g of each of the samples under a pressure of 20 kg$_f$/cm$^2$.

TABLE 1

| Sample | Example 1 | Comparative Example 1 |
|---|---|---|
| Hardness (kgf/cm$^2$) | 7.7 | 1.4 |

As can be seen from the results in Table 1 above, the cotton-like material of Comparative Example 1 had too low a hardness to be formulated into a mask pack. In contrast, the cotton-like material of Example 1 according to the present invention showed a hardness that was about 5.5-times higher than that of Comparative Example 1, such that it could be formulated into a mask pack.

TEST EXAMPLE 2

Water-Holding Effect of Cosmetic Cotton-Like Material

First, a constant temperature and constant humidity chamber was installed in order to measure the movement of water. Test samples of about 0.5-2 g of each of the cotton-like material prepared from paper mulberry in Example 1 and commercially available cotton-like cellulose (manufactured by Nippon Paper Chemical Co. Ltd., Japan), were each loaded into the open portion of the top of a water-permeable cup, and the water-permeable cup was placed in the chamber. The samples were tested in two lots for reproducibility Samples 1 and 2 comprised the cotton-like materials prepared in Example 1, and Samples 3 and 4 comprised the general cellulose powder. The general cellulose powder was powder prepared using cellulose from general wood material. The test was conducted on the assumption that the internal temperature would be higher than the external temperature.

The internal humidity of the cup was maintained at a relative humidity of 75% by a saturated aqueous solution of potassium chloride, and the humidity of the constant temperature and constant humidity chamber was maintained at a relative humidity of 25% by a saturated aqueous solution of magnesium chloride. When vapor flowing from the internal area to the external area occurred, the amount of water held in the cotton-like material prepared from paper mulberry was measured. The reason for measuring the water absorption of the cotton-like paper mulberry material present at the boundary when the movement of vapor occurs is because the external area is an infinite space, and thus it can be supposed that, even when the internal vapor is added to the external area, a change in the external humidity does not occur.

The inside of the cup can be defined as an internal system, and the constant temperature and constant humidity chamber outside the cup can be defined as an external system. Because the amount of vapor in the internal system is greater than that in the external system, vapor will move from the internal system to the external system according to the difference of partial vapor pressure between the two systems. At this time, the vapor will pass through the boundary between the internal system and the external system. That is, the vapor will pass through the cotton-like paper mulberry material present at the boundary. The amount of vapor passing through the boundary was determined by measuring the weight of the cup with an electronic balance at one-hour intervals after about 2 hours when the internal system and the external system could reach a stable state. The measurement results are shown in Table 2 below.

TABLE 2

Comparison of water-absorbing capacity between samples

| Sample | F [g/h] | F' [g/m² h] | R [m² h mmHg/g] |
|--------|---------|-------------|-----------------|
| #1 | 0.171 | 39.76 | 0.265 |
| #2 | 0.181 | 42.09 | 0.250 |
| #3 | 0.123 | 28.6 | 0.3680 |
| #4 | 0.121 | 29.13 | 0.3740 |

[Samples 1 and 2: cotton-like material prepared from paper mulberry; and Samples 3 and 4: general cotton-like cellulose material (manufactured by Nippon Paper Chemical Co. Ltd, Japan)]

F in Table 2 is the average hourly amount of moisture absorption of the sample having a volume of 0.0043 $m^2$, measured at 2 hours after the start of the test when the moisture absorption becomes constant. F' in Table 2 is the amount of moisture absorption per unit area, calculated from the average hourly amount. In the results in Table 2 above, Samples 1 and 2 had similar moisture absorption amounts and showed moisture-absorbing capacities that were about 400 higher than those of Samples 3 and 4. Such results suggest that the cotton-like material prepared from paper mulberry, a raw material for Korean traditional paper, showed excellent water-absorbing capacity compared to other kinds of cotton-like material. The reason is considered to be attributable to the characteristic complex fine fibrous texture of paper mulberry.

EXAMPLE 2

Preparation of Mask Pack Using Cosmetic Cotton-Like Material

Polyacrylic acid was completely dissolved in an aqueous phase at a concentration of 5% (w/w). The polymer compound agar was added to the solution at a concentration of 0.2% (w/w), and the mixture was boiled by heating to 100° C. and stirred. The stirred solution was cooled to 70° C. and oil as a softener was added thereto. Then, skin active ingredients were added to the resulting mixture at a temperature lower than 50° C. As the skin active ingredients, commercially known ingredients for reducing wrinkles, whitening the skin and improving skin troubles and keratin were added within acceptable content ranges.

The cosmetic cotton-like material prepared in Example 1 was soaked in the active ingredient-containing solution. The soaked cosmetic cotton-like material was attached and fixed to a nonwoven fabric, thus preparing a mask pack of Example 2.

COMPARATIVE EXAMPLE 2

A mask pack of Comparative Example 2 was prepared according to the same method as that of Example 2, except that the cotton-like material prepared in Comparative Example 1 was used instead of the cotton-like material prepared in Example 1.

COMPARATIVE EXAMPLE 3

A mask pack of Comparative Example 3 was prepared according to the same method as that of Example 2, except that the commercially available cotton-like cellulose material (manufactured by Nippon Paper Chemical Co. Ltd, Japan) was used instead of the cotton-like material prepared in Example 1.

TEST EXAMPLE 3

Sensory Evaluation

To evaluate the skin feel of the mask packs prepared in Example 2 and Comparative Examples 2 and 3, twenty 20-30 year-old women used the mask packs. Then, sensory evaluation for skin peel and air permeability upon pack adhesion and a moist feel after pack removal was conducted on one of 5-point, 7-point or 9-point scale, as defined below. The evaluation results are shown in Table 3 below.

TABLE 3

| Test Material | Skin Feel Upon Pack Adhesion | Air Permeability | Moist Feel After Pack Removal |
|---------------|------------------------------|------------------|-------------------------------|
| Example 2 | 7 | 3 | 7 |
| Comp. Ex. 2 | 5 | 3 | 3 |
| Comp. Ex. 3 | 3 | 1 | 1 |

(Skin feel upon pack adhesion: 7-point scale of 1, 3, 5 and 7; air permeability: 5-point scale of 1, 3 and 5; and moist feel after pack removal: 9-point scale of 1, 3, 5, 7, and 9)

As can be seen from the results in Table 3 above, the mask pack of Example 2 prepared using the cotton-like material according to the present invention was excellent in skin feel, air permeability and moist feel compared to the mask packs of Comparative Examples 2 and 3.

The invention claimed is:

1. A method for preparing a cosmetic cottony material from paper mulberry, the method comprising the steps of:
   1) treating the bark of paper mulberry with an alkaline solution to remove the black outer bark from the paper mulberry bark;
   2) bleaching the paper mulberry bark, from which the black outer bark has been removed, with a bleaching agent, to prepare a white bark;
   3) adding an alkaline solution to the white bark to obtain a paper mulberry bast fiber, and pulping the paper mulberry bast fiber;
   4) washing and drying the pulped paper mulberry bast fiber; and
   5) hydrolyzing the dried paper mulberry bast fiber with an acid while maintaining the bast fiber at a temperature of 30° C. to 40° C. for more than 48 hours, to obtain the cosmetic cottony material.

2. The method of claim 1, wherein the alkaline solution is at least one selected from the group consisting of aqueous solutions of sodium hydroxide, ammonium hydroxide and copper hydroxide.

3. The method of claim 1, wherein the bleaching agent is at least one selected from the group consisting of calcium hypochlorite, sodium hypochlorite and sodium chlorite.

4. The method of claim 1, wherein the hydrolyzing step is performed in 1-3N aqueous solution of hydrogen chloride at a temperature of 30° C. to 40° C. for 48-60 hours.

5. A method for preparing a mask pack, comprising the steps of:
   1) treating the bark of paper mulberry with an alkaline solution to remove the black outer bark from the paper mulberry bark;
   2) bleaching the paper mulberry bark, from which the black outer bark has been removed, with a bleaching agent, to prepare a white bark;
   3) adding an alkaline solution to the white bark to obtain a paper mulberry bast fiber, and pulping the paper mulberry bast fiber;
   4) washing and drying the pulped paper mulberry bast fiber;
   5) hydrolyzing the dried paper mulberry bast fiber with an acid while maintaining the bast fiber at a temperature of 30° C. to 40° C. for more than 48 hours, to obtain a cosmetic cottony material; and
   6) mixing the cosmetic cottony material with a skin active ingredient to prepare a mask pack.

6. The method of claim 5, wherein the alkaline solution is at least one selected from the group consisting of aqueous solutions of sodium hydroxide, ammonium hydroxide and copper hydroxide.

7. The method of claim 5, wherein the bleaching agent is at least one selected from the group consisting of calcium hypochlorite, sodium hypochlorite and sodium chlorite.

8. The method of claim 5, wherein the hydrolyzing step is performed in 1-3N aqueous solution of hydrogen chloride at a temperature of 30° C. to 40° C. for 48-60 hours.

9. The method of claim 5, wherein the skin active ingredient comprises at least one of a wrinkle-reducing ingredient selected from the group consisting of retinol, retinyl palmitate, adenosine, and polyethoxylated retinamide; a skin whitening ingredient selected from the group consisting of arbutin, a paper mulberry extract, a licorice extract, ethyl ascorbyl ether, ascorbyl glucoside, and magnesium ascorbyl phosphate; a moisturizing ingredient selected from the group consisting of *Schizophyllum commune* polysaccharide, niacinamide, and N-acetylglucosamine; and a skin trouble- and keratin-improving ingredient selected from the group consisting of an ivy extract, a fancy extract, a Chamomile extract, and a soybean extract.

10. The method of claim 5, wherein the cosmetic cottony material and the skin active ingredient are mixed with each other at a weight ratio of 1:10 to 10:1.

* * * * *